United States Patent [19]

Holmes et al.

[11] Patent Number: 4,873,990

[45] Date of Patent: Oct. 17, 1989

[54] CIRCUMFERENTIAL PRESSURE PROBE

[75] Inventors: Harlan K. Holmes, Newport News; Thomas C. Moore, Jr., Poquoson; Andrew J. Fantl, Richmond, all of Va.

[73] Assignees: The United States of America as represented by the Administrator of the National Aeronautics and Space Administration, Washington, D.C.; Virginia Commonwealth University, Richmond, Va.

[21] Appl. No.: 248,020

[22] Filed: Sep. 23, 1988

[51] Int. Cl.⁴ ............................................. A61B 5/00
[52] U.S. Cl. .................................. 128/748; 128/675; 128/778
[58] Field of Search .................... 128/748, 672–675, 128/774, 778, 780; 73/753–754, 756, 736, 716

[56] References Cited

U.S. PATENT DOCUMENTS

| 4,349,033 | 9/1982 | Eden | 128/774 X |
|---|---|---|---|
| 4,456,013 | 6/1984 | DeRossi et al. | 128/675 |
| 4,484,585 | 11/1984 | Baier | 128/748 |
| 4,557,269 | 12/1985 | Reynolds et al. | 128/675 |
| 4,566,465 | 1/1986 | Arhan et al. | 128/778 |
| 4,589,287 | 5/1986 | Dickens | 73/727 |
| 4,711,246 | 12/1987 | Alderson | 128/667 |
| 4,711,249 | 12/1987 | Brooks | 128/748 |
| 4,722,347 | 2/1988 | Ligtenberg et al. | 128/675 |

Primary Examiner—Kyle L. Howell
Assistant Examiner—Angela D. Sykes
Attorney, Agent, or Firm—George F. Helfrich; John R. Manning; Charles E. B. Glenn

[57] ABSTRACT

A probe for measuring circumferential pressures inside a body cavity. In the preferred embodiment, a urodynamic pressure measurement probe for evaluating human urinary sphincter function is disclosed. Along the length of the probe are disposed a multiplicity of deformable wall sensors (15) which typically comprise support tube sections (55) with flexible side wall areas (57, 16). These are arranged along the length of the probe in two areas, one just proximal to the tip (13) for the sensing of fluid pressure inside the bladder, and five in a sensing section (14) which is positioned within the urethra at the point at which the urinary sphincter constricts to control the flow of urine. The remainder of the length of the probe comprises multiple rigid support tube sections (10) interspersed with flexible support tube sections in the form of bellows (58) to provide flexibility.

5 Claims, 2 Drawing Sheets

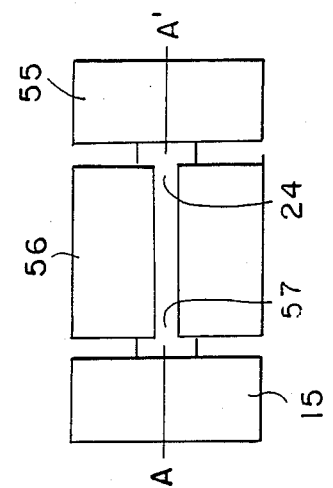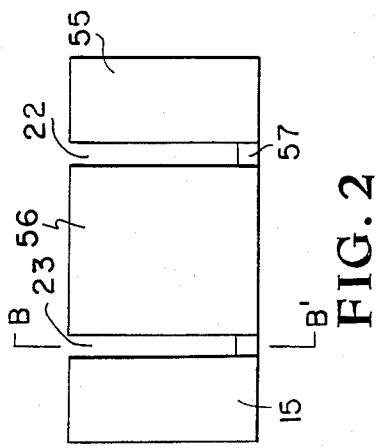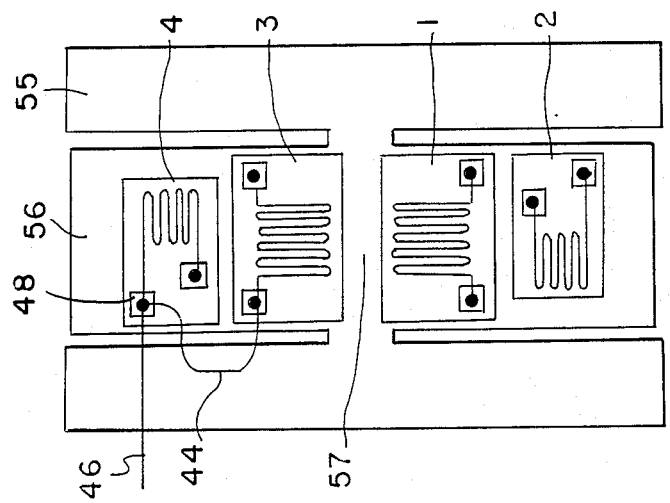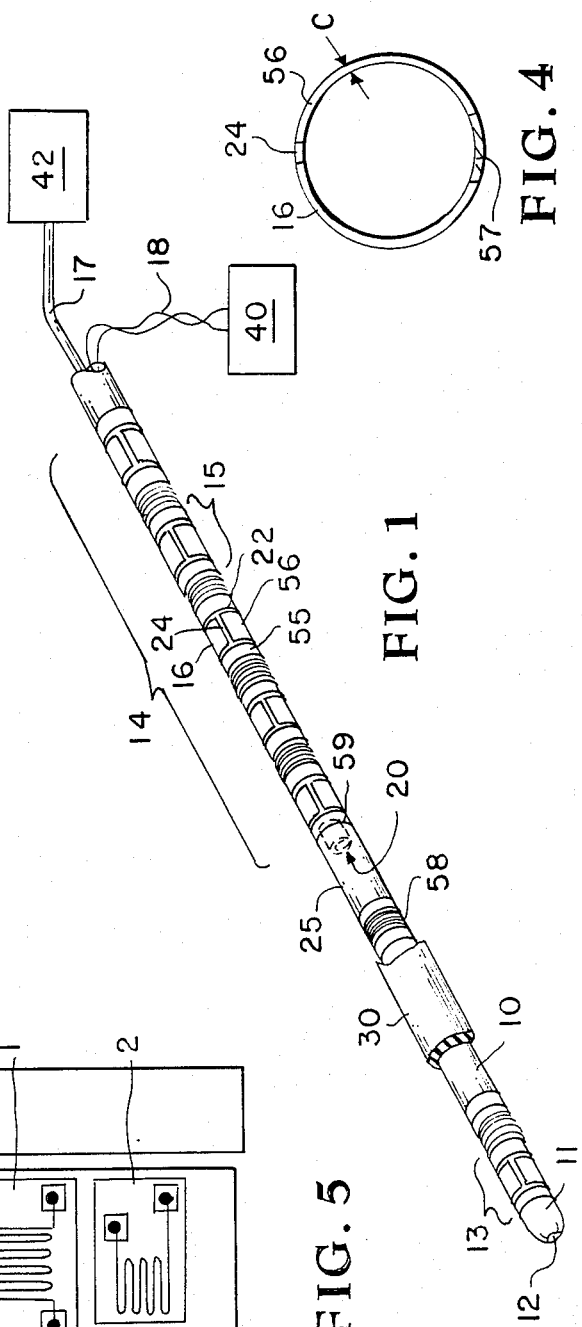

CIRCUMFERENTIAL PRESSURE PROBE

ORIGIN OF THE INVENTION

The invention described herein was jointly made by employees of the United States Government and by an employee of the Medical College of Virginia, Virginia Commonwealth University. It may be manufactured or used by or for the Government for governmental purposes without payment of any royalties thereon or therefor.

TECHNICAL FIELD OF THE INVENTION

This invention relates to the measurement of pressures inside body cavities and more particularly to a probe which is able to respond to pressures on it around its entire periphery and at multiple points along its length.

BACKGROUND OF THE INVENTION

Medical practice often requires the measurement of subtle pressure changes inside the body, and many different means have been devised to determine these values. Particular interest has been devoted to the determination of pressures inside such structures as the urethra and the coronary arteries.

When fluid filled catheters are used to convey pressure to sensors located outside the body, a variety of errors result from extraneous parameters such as air temperature, catheter length, atmospheric pressure, and patient position. The recent development of miniaturized strain gauged elements, where the entire sensor can be inserted into the body cavity, has helped to control some of these variables. However, since most sensors rely on a single instrumented surface, they are peculiarly sensitive to rotational effects which cause the reported pressure to vary widely from the true circumferential pressure due to localized blocking of all or a part of the element. Brooks describes a method of measuring circumferential pressure in U.S. Pat. No. 4,711,249, but the substantial blocking of the lumen of the supporting tube by the transverse location of the sensing elements limits its effectiveness in certain applications.

A particular area of interest for measurement of circumferential pressures is in the evaluation of the human urinary sphincter and the quantification of its effectiveness in controlling the flow or urine. In evaluating the urinary sphincter, a series of pressure measurements must be taken along the length of the urethra where it is surrounded by the sphincter muscle. At the same time, the fluid pressure inside the bladder must be measured so that the ability of the sphincter to close the urethra to the passage of the urine can be determined. Prior technology for obtaining a urethral pressure profile involves the insertion of a catheter incorporating two pressure sensors, the first sensor measuring bladder pressure and the second measuring pressure at a fixed location relative to the first. The profile is obtained by moving the catheter at a controlled rate and recording the pressures.

The accuracy of the profile is facilitated by the ability to withdraw urine from the bladder or introduce fluid into it so as to control bladder distension during a series of tests. Additionally, the ability to make all measurements simultaneously is highly desirable, since transient events such as coupling or muscular exertion are not accurately reproducible for serial measurements of pressures in differing locations.

All of the foregoing functions must be performed by a urodynamic pressure measurement probe that is small enough to fit within a normal urethra without causing undue distension of the surrounding tissue, is protected from corrosive and electrically conductive urine, and is rugged, easily sterilized and electronically stable. If it is too large or irregularly shaped the device will produce false pressure readings as well as inducing discomfort in the patient being tested. If it generates discomfort, its efficacy will be limited due to failure of the patient to cooperate when required to bear down, cough or more.

Therefore, an object of the present invention is to provide a sensor for the measurement of circumferential pressures inside body cavities, thereby removing the measurement errors introduced by sensors which only measure pressure at a discrete point or aperture.

A further object of the present invention is to provide a urodynamic pressure measuring probe in the form of a thin catheter with multiple circumferential pressure sensors along its length, thereby allowing a pressure profile to be obtained without moving the catheter.

A further object of the present invention is to provide a urodynamic pressure measuring probe which is compact, lightweight and durable so that it may be connected to a telemetry system for monitoring patients during normal activities.

BRIEF SUMMARY OF THE INVENTION

According to the invention, the foregoing and additional objects are attained by a probe with one or more deformable wall sensors along its length which can be inserted into the area under investigation and which will return an electrical signal proportional to the pressure on the external surface of the probe.

Deformable wall sensors comprise moveable wall sections of the supporting probe tube and a means to modulate a signal as the wall of the probe moves under the influence of an external pressure.

In the preferred embodiment, the generalized form of the invention is realized as follows:

A urodynamic pressure measurement probe with an outside diameter small enough to be placed in a human urethra is instrumented with a series of deformable wall sensors along its length. These sensors are placed so as to be within the urinary sphincter when the probe is in place, and they are sensitive to the range of pressures exerted by the sphincter.

The deformation of the walls of each sensor is determined by the modification of an excitation signal as it passes through four strain gauges arranged in a four-element resistance bridge configuration.

An additional sensor is placed at the tip of the probe to sense the fluid pressure of the urine in the bladder, and an internal tube passes down the length of the probe to allow the probe to also function as a catheter for the introduction of substances into the bladder or extraction of urine from the bladder.

The probe has a means for connecting the sensors to control and recording circuits. The probe also has a second inner tube forming a lumen for the introduction or extraction of fluids from the bladder.

Overall bending of the probe is provided by multiple short flexible support tube sections placed along the length of the probe.

The entire probe is covered with a thin elastic sheath which protects the sensors from contamination and provides an easily sterilizable and non-irritating surface.

BRIEF DESCRIPTION OF THE DRAWINGS

FIG. 1 is a side view of the preferred embodiment of the urodynamic pressure measurement probe.

FIG. 2 is a side view of a typical deformable wall sensor section of a support tube as used in the urodynamic pressure measurement probe shown in FIG. 1.

FIG. 3 is a top view of a typical deformable wall sensor section of a support tube as used in the urodynamic pressure measurement probe shown in FIG. 1.

FIG. 4 is a sectional view of a typical deformable wall sensor section of a support tube taken along line B—B' of FIG. 2.

FIG. 5 is an internal layout plan of a typical deformable wall sensor showing positioning for strain gauges. View is a two-dimensional plan of the interior surface after sectioning along lines A and A' of FIG. 3.

DETAILED DESCRIPTION OF THE INVENTION

Figure 6:
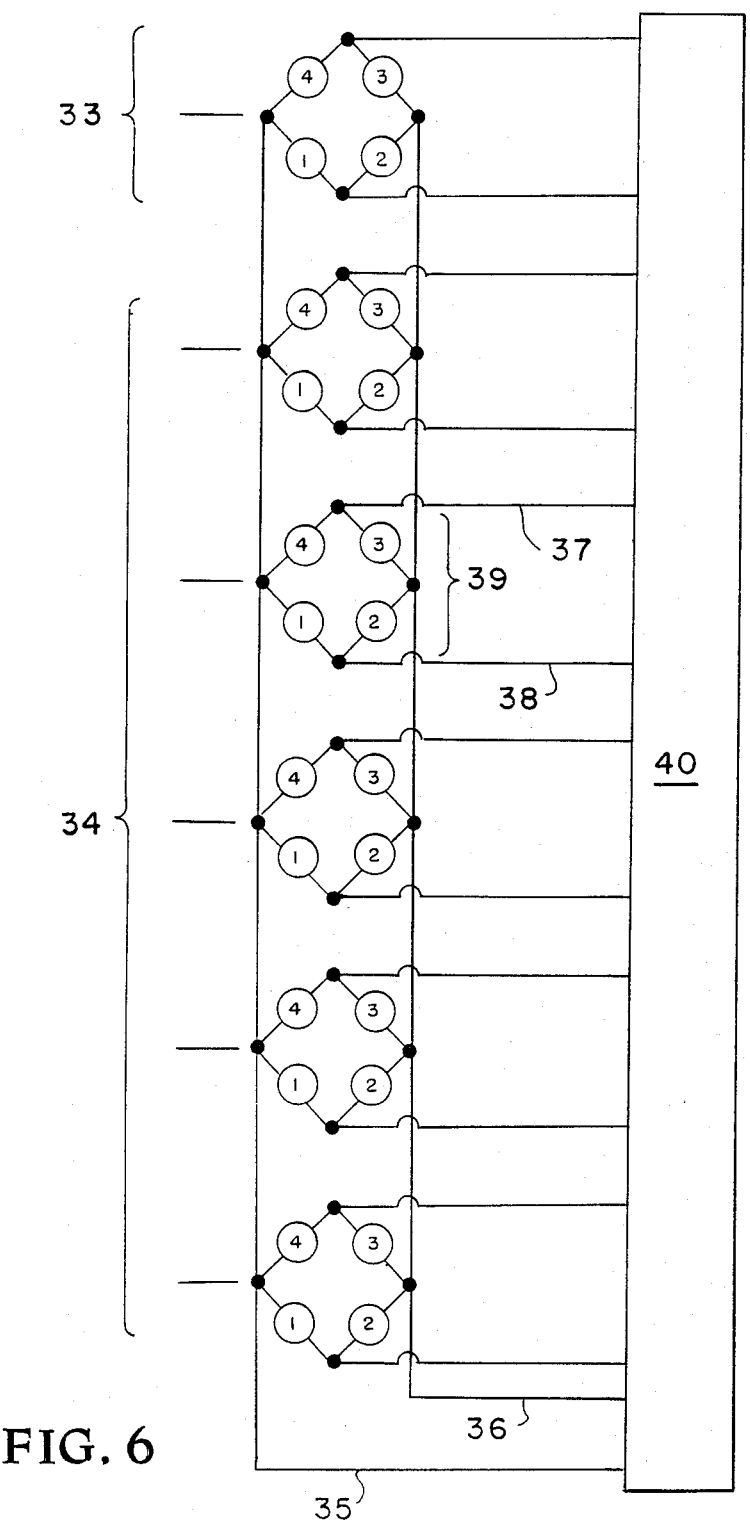
FIG. 6 is a schematic of the connections necessary for the urodynamic pressure measurement probe shown in FIG. 1.

The invention in general is a probe for measuring circumferential pressures inside a cavity. The most likely fields of application for this probe are in medical diagnostic measurements of intravascular pressures and evaluations of sphincter closing pressures.

FIG. 1 shows the preferred embodiment of the invention as a urodynamic pressure measurement probe (25). Along its length are disposed a multiplicity of deformable wall sensors (15) which typically comprise support tube sections (55) with flexible wall sections (56, 16). These are arranged along the length of the probe in two sections, one just proximal to the tip (13) for the sensing of fluid pressure inside the bladder, and five in a sensing section (14) which is positioned within the urethra at the point at which the urinary sphincter constricts to control the flow or urine. The remainder of the length of the probe comprises multiple rigid support tube sections (10) interspersed with flexible support tube sections in the form of bellows (58) to provide flexibility. Connections between support tube joints are formed by connecting sections (59) and solder.

In the preferred embodiment all support tubes consist of 304 stainless steel, but obviously other materials of similar rigidity and elasticity could be substituted. The distal end of the probe is terminated by a rounded tip (11) which has a central passageway (12) communicating with the lumen of a second inner tube (17). The entire probe is covered with a thin flexible covering (30) which seals the slots (22, 24) in the sensors so that fluids can not enter the interior of the probe. This covering is also sterilizable and non-irritating.

The second inner tube (17) passes through the lumen of the probe (20) and at the proximal end of the second tube is a connector (42) suitable for connection to external suction or pressure means such as a syringe. The wires (18) which connect the deformable wall sensors (15) to external control circuitry (40) also pass through the lumen of the probe (20).

FIG. 2 and FIG. 3 show a typical deformable wall sensor (15) with transverse slots (22, 23) extending most of the way through the support tube (55) leaving only a narrow bottom segment (57). Also shown is a longitudinal slot (24) connecting the transverse slots on that two flexible wall areas (56, 16) are separated from the support tube on three sides, remaining affixed only on a single side along the bottom segment (57). The thickness of the flexible wall area must be reduced uniformly until the dimension marked as C in FIG. 4 is thin enough to allow flexing under the pressures expected in the cavity being measured. For the human urinary sphincter and bladder pressure measurements, a flexible wall thickness (dimension C in FIG. 4) of approximately 0.004 inches when the support tube consists of 304 stainless steel is effective throughout the expected pressure measurement range of zero to 250 centimeters of water (cm $H_2O$).

FIG. 5 shows the arrangement of four strain gauges (1, 2, 3 & 4) on the inner surface of a typical deformable wall sensor which has been split along lines A and A' of FIG. 3 and opened so as to display a two-dimensional plan view. One of the connecting wires (44) between strain gauges is shown, along with a representative external connection wire (46) and the solder joint connection (48) between the two.

FIG. 6 portrays a wiring diagram for the urodynamic pressure measurement probe (25) showing the positive (35) and negative (36) excitation connections and the positive (37) and negative (38) signal connections for a typical sensor (39). Section (33) portrays the wiring for the bladder pressure sensor (13) and suction (34) portrays the wiring for the sphincter pressure sensing section (14). All sensor wires lead to a connection to external control and measurement means (40). In practice, these generally comprise a power supply, amplifiers and strip chart recorders. However, this invention can also be practiced with the external connection (40) being a telemetry device transmitting to remote monitoring equipment.

The proximal end of the probe can be terminated in any manner appropriate for medical equipment which will allow connection of the wires from the sensors to be attached to external control and sensing circuitry. The inner tube which allows the probe to function as a catheter can be terminated in any manner which will allow the attachment of devices such as syringes for the introduction of substances into the bladder or extraction of urine from the bladder via the probe.

Although specific embodiments of the invention have been described herein, they are to be considered exemplary of the novel features thereof and are not exhaustive. There are obviously many variations and modifications of these specific examples that will be readily apparent to those skilled in the art in light of the above teachings without departing from the spirit or scope of the appended claims. It is, therefore, to be understood that the invention may be practiced otherwise than is specifically described.

What is claimed as new and desired to be secured by Letters Patent of the United States is:

1. A probe for measuring circumferential pressures inside a body cavity comprising:
   a circularly sectioned, longitudinally extended support tube, said support tube having an internal lumen and an outside wall, said outside wall consisting of an elastic material, said material capable of being deformed by pressures in the range expected to exist in the area inside the body cavity which is under investigation and tending to return to its original configuration once the pressure is removed, at least one deformable wall sensor along the length of the support tube, each such sensor comprising:

slot means extending through the outside wall of the support tube so that an essentially rectangular flexible wall section is separated from the support tube on three sides, the fourth side of the flexible wall section remained attached longitudinally to the support tube; and deformation measurement means such that when the flexible wall section is displaced inwardly by an externally applied pressure and deformed, a signal proportional to the degree of deformation is produced which is detectable by an external sensing means;

external connecting means for connecting the deformable wall sensor to an external sensing means, said external connecting means passing through the lumen of the support tube and terminating at a connection with the external sensing means; and protecting means for protecting sensor components from substances in the area inside the body cavity which is under investigation so that said substances cannot penetrate the slot means.

2. A probe as in claim 1 which additionally comprises a second tube, said second tube adding the functionality of a catheter to the probe, said second tube passing through the lumen of the support tube, said second tube communicating with the area inside the body cavity which is under investigation, said second tube terminating outside the proximal end of the probe in an attachment means so that said second tube can be connected to an external fluid exchange means; and said second tube being of a size and constructed of material suitable for exchanging diagnostic substances between the area inside the body cavity which is under investigation and the attachment means.

3. A probe as in claim 1, wherein the deformable wall sensor comprises:

a flexible wall area formed by two transverse slot means spaced longitudinally along the support tube, said transverse slot means being connected with a single longitudinal slot means positioned so as to bisect each of the transverse slot means, thereby forming two equal and opposed rectangular flexible wall sections;

deformation measurement means comprising four strain gauges, two such gauges affixed to the inner surface of each of the flexible wall sections;

additional connecting means by which the four strain gauges are arranged into a four-element resistance bridge configuration; and contact means where the additional connecting means contact the external connecting means.

4. A probe according to claim 2, which is specifically adapted to the anatomy of the urinary tract of a human for urodynamic pressure measurement, wherein, there is a multiplicity of deformable wall sensors having flexible wall areas covering at least 75 percent of the circumference of the support tube at the point at which external pressure is detected so as to provide a measurement of true circumferential pressure;

each deformable wall sensor detects pressure differences as small as five percent (5%) in the range between Zero cm $H_2O$ and 250 cm $H_2O$;

there is a sensing section comprising multiple deformable wall sensors so as to provide several measurements of urinary sphincter closing pressure over the expected length of the sphincter;

there is an additional sensor positioned at the distal end of the probe and separated from the sensing section, so that fluid pressure in the bladder of the human can be measured while the sensing section is positioned in the urethra of the human;

there is a number of flexible support tube sections such that the probe can bend gradually over a substantial portion of its length; and the protecting means comprises a continuous, flexible, tubular covering, said covering sealed to the outside of each support tube section so as to close all slot means, said covering having an external diameter essentially the same as the external diameter of the support tube so as to fit closely yet avoid compressing the flexible wall sections, and said covering being non-irritating and impervious to bodily fluids.

5. A urodynamic pressure measurement probe as in claim 4, wherein each of the deformable wall sensors comprise:

a flexible wall area formed by two transverse slot means spaced longitudinally along the support tube, said transverse slot means being connected with a single longitudinal slot means positioned so as to bisect each of the transverse slot means, thereby forming two equal and opposed rectangular flexible wall sections, deformation measurement means comprising four strain gauges, two such gauges affixed to the inner surface of each of the flexible wall sections;

additional connecting means by which the four strain gauges are arranged into a four-element resistance bridge configuration; and contact means where the additional connecting means contact the external connecting means.

* * * * *